(12) United States Patent
Park et al.

(10) Patent No.: US 9,404,808 B2
(45) Date of Patent: Aug. 2, 2016

(54) TEMPERATURE AND TIME INDICATOR FOR CONFIRMING HIGH PRESSURE STERILIZATION

(71) Applicants: Intellectual Discovery Co., Ltd., Seoul (KR); Inditechkorea Co., Ltd., Hwaseong-si, Gyeonggi-do (KR)

(72) Inventors: Jihoon Park, Suwon-si (KR); Gilnam Hong, Seoul (KR); Misup Lee, Pyeongtaek-si (KR)

(73) Assignees: Intellectual Discovery Co., Ltd., Seoul (KR); InditechKorea Co., Ltd., Hwaseong-si (KR)

( * ) Notice: Subject to any disclaimer, the term of this patent is extended or adjusted under 35 U.S.C. 154(b) by 176 days.

(21) Appl. No.: 14/259,438

(22) Filed: Apr. 23, 2014

(65) Prior Publication Data

US 2014/0311400 A1    Oct. 23, 2014

(30) Foreign Application Priority Data

Apr. 23, 2013 (KR) ........................ 10-2013-0044869

(51) Int. Cl.

| | | |
|---|---|---|
| G01K 1/02 | (2006.01) | |
| G01K 3/04 | (2006.01) | |
| A61L 2/28 | (2006.01) | |
| G01K 5/02 | (2006.01) | |
| G01K 5/04 | (2006.01) | |
| G01K 5/12 | (2006.01) | |
| G01D 21/00 | (2006.01) | |

(52) U.S. Cl.
CPC ... G01K 3/04 (2013.01); A61L 2/28 (2013.01); G01D 21/00 (2013.01); G01K 1/02 (2013.01); G01K 5/02 (2013.01); G01K 5/04 (2013.01); G01K 5/12 (2013.01); G01K 2207/04 (2013.01)

(58) Field of Classification Search
CPC ............. G01K 1/02; G01K 5/02; G01K 5/04; G01K 5/12; G01K 2207/04; G01K 3/04; G01D 21/00
USPC .......... 116/206–207, 216–220; 374/102, 104, 374/106, 159–162; 422/50, 82.12, 119, 425
See application file for complete search history.

(56) References Cited

U.S. PATENT DOCUMENTS

| | | | | |
|---|---|---|---|---|
| 4,280,361 | A * | 7/1981 | Sala ........................ | G01K 11/06 116/216 |
| 4,390,291 | A * | 6/1983 | Gaven, Jr. .............. | G01K 11/08 116/217 |
| 4,469,452 | A * | 9/1984 | Sharpless ............... | C09K 19/58 116/206 |
| 6,030,118 | A * | 2/2000 | Schneider .............. | G01K 11/06 116/204 |
| 6,848,390 | B2 * | 2/2005 | Akers ..................... | G01K 5/483 116/216 |
| 7,490,575 | B2 * | 2/2009 | Taylor .................... | G01K 3/005 116/207 |
| 7,891,310 | B2 * | 2/2011 | Taylor .................... | G01K 3/005 116/216 |
| 8,061,294 | B2 * | 11/2011 | Suda ....................... | G01K 11/06 116/216 |
| 8,707,887 | B2 * | 4/2014 | Suda ....................... | G01K 11/06 116/216 |

* cited by examiner

*Primary Examiner* — R. A. Smith
*Assistant Examiner* — Tania Courson
(74) *Attorney, Agent, or Firm* — NSIP Law

(57) ABSTRACT

Provided is a temperature and time indicator for confirming sterilization, and more particularly, a temperature and time indicator for confirming sterilization including a development material member, a development medium member, a blocking member, and first and second forming sheets, such that whether medicines or milk products pass through a high temperature sterilization process performed under a regulated temperature and pressure condition is indicated through a sterilization confirming mark to the outside.

7 Claims, 4 Drawing Sheets

FIG. 4
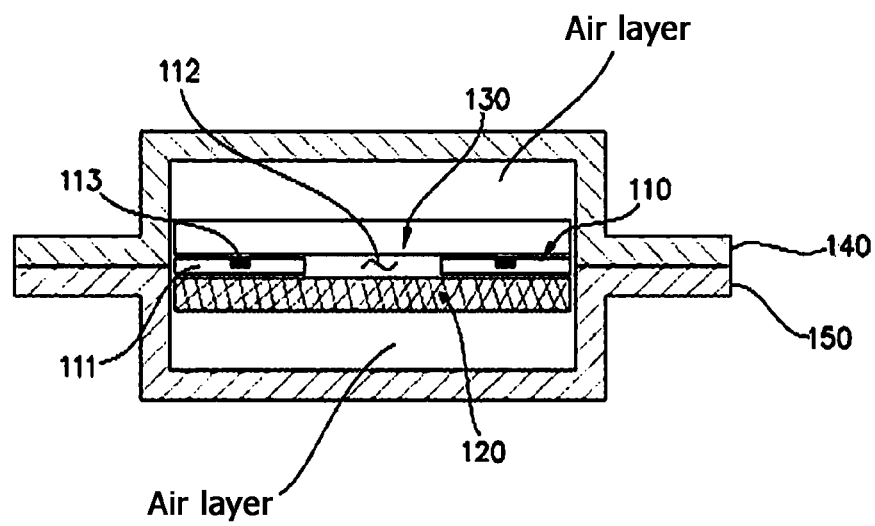
(a)
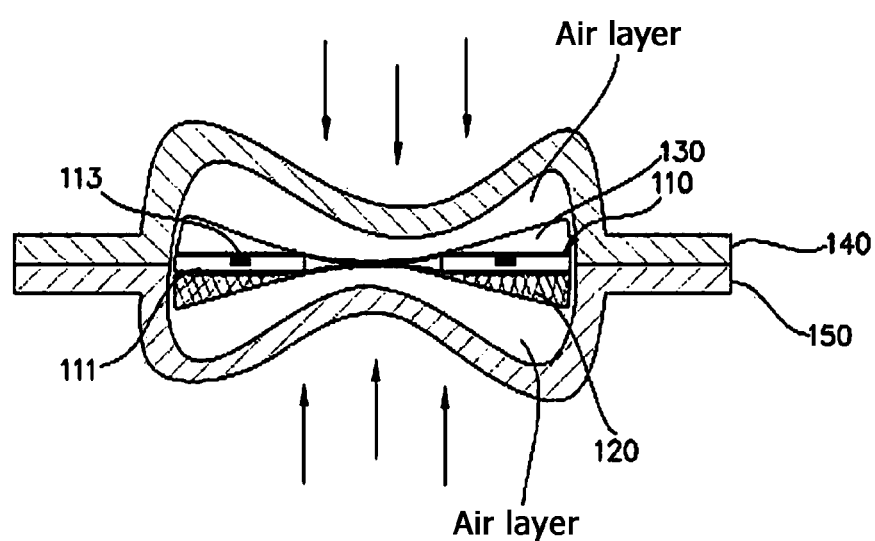
(b)

TEMPERATURE AND TIME INDICATOR FOR CONFIRMING HIGH PRESSURE STERILIZATION

CROSS-REFERENCE TO RELATED APPLICATION

This application claims priority to and the benefit of Korean Patent Application No. 10-2013-0044869, filed on Apr. 23, 2013, the disclosure of which is incorporated herein by reference in its entirety.

BACKGROUND

1. Field of the Invention

The present invention relates to a temperature and time indicator for confirming high pressure sterilization, and more particularly, to a temperature and time indicator for confirming high pressure sterilization such that whether a product that necessarily requires a high pressure sterilization process such as medicines or foods passes through the high pressure sterilization process performed at a regulated temperature and pressure condition is indicated to be seen from the outside through a specified mark.

2. Discussion of Related Art

In recent times, as a refrigeration and freezing industry is advanced, foods and medicines that require freezing and refrigeration should be appropriately managed, and in particular, the medicines or foods that require a strict temperature management during distribution should be always maintained in a fresh state during the entire distribution from producers to consumers. In particular, when the medicines are exposed to a non-defined temperature for a specified time or more, since an ingredient may be spoiled to cause a serious medical side effect to a user, it is very important for the consumer to visually check a distribution process of the medicines. This may be applied to all products that can be easily spoiled according to a variation in temperature like foods as well as the medicines.

In addition, among medical instruments, foods, metal products, glass products, paper or textile products, water, media, reagents and liquid medicines, products in which germs may propagate should pass through a high pressure sterilization process as long as the products can endure a high temperature and a high pressure.

Here, the high pressure sterilization process refers to a sterilization process of exposing products under a condition of a temperature of about 121 degrees and a pressure of about 15 psi for about 15 minutes to destroy all of nurse cells and endospores present in the products and effectively coagulate bacteria.

However, it is difficult for consumers in a final consumption step to visually check in a purchase step whether the medicines or foods are distributed, stored and handles under regulated temperature management or pass through an appropriate high pressure sterilization process, but the consumers can only determine whether the products is correctly stored after seeing the current storage state and appearance of the products. Further, it is also difficult for a professional manager who manages these products to visually check whether the products are distributed, stored and handles under the regulated temperature management condition or pass through the appropriate high pressure sterilization process.

Accordingly, a plurality of methods and apparatuses for allowing a consumer to determine whether the products are distributed under the regulated temperature management are disclosed, a temperature and time indicator (TTI) (an instrument or a label attached to each of the medicines or milk products and configured to display accumulated temperature and time records in the products) is used by an international major company such as 3M or the like, and various kinds of TTIs are developed and used.

However, there are no method and apparatus for allowing a consumer to determine whether the products pass through an appropriate high pressure sterilization process under regulated temperature and pressure management, other than whether the products are distributed under regulated temperature management.

Accordingly, the inventor(s) has invent a temperature and time indicator for confirming sterilization, which is capable of allowing a consumer to visually check whether the products that necessarily require the high pressure sterilization process pass through the high temperature sterilization process performed under a regulated temperature and pressure condition through a specific mark.

SUMMARY OF THE INVENTION

In order to solve the above-mentioned problems, the present invention is directed to provide a temperature and time indicator for confirming high pressure sterilization capable of allowing a consumer to check whether products that necessarily require a high pressure sterilization process pass through the high temperature sterilization process performed under a regulated temperature and pressure condition.

In addition, the present invention is directed to provide a temperature and time indicator for confirming high pressure sterilization capable of (i) accommodating and sealing a development material member, a development medium member and a blocking member therein, (ii) protecting the development material member, the development medium member and the blocking member from an external impact, and (iii) being adhered and deformed under a specific pressure condition to start activation thereof, by providing first and second forming sheets.

Further, the present invention is directed to provide a temperature and time indicator for confirming sterilization capable of allowing a user to visually check whether a high temperature sterilization process performed under a regulated temperature and pressure condition is performed, by providing a development material melted under a specific temperature condition, a development material member configured to absorb and diffuse the development material, and a blocking member, which functions as a diffusion path of the corresponding development material, configured to allow the corresponding diffusion to be checked from the outside.

The present invention is directed to a temperature and time indicator for confirming sterilization including: a development material member melted when exposed to a specific temperature; a development medium member configured to absorb and diffuse the development material member; a blocking member disposed between the development material member and the development medium member; and first and second forming sheets configured to accommodate the development material member and the development medium member in upper and lower sides, wherein the first and second forming sheets are compressed and adhered when exposed to a specific pressure, and a development material comes in contact with the development medium member through a through-hole formed in the blocking member to start activation thereof.

Preferably, the blocking member may further include a through-hole through which any one or more of the development material member and the development material passes.

Preferably, the blocking member may have a specific pattern or form printed along an outer circumferential surface of the through-hole.

Preferably, the development material member may correspond to a type in which the development material that is able to be melted at a specific temperature is absorbed into nonwoven fabric.

Preferably, the development medium member may be formed of a micro-porous film and become transparent when come in contact with the development material.

Preferably, the first and second forming sheets may have adhered surfaces formed at portions thereof, and the adhered surfaces may seal the development material member and the development medium member at upper and lower sides.

Preferably, the first and second forming sheets may not be spoiled and deformed even when exposed to a temperature at which the development material is able to be melted.

The temperature and time indicator for confirming high pressure sterilization according to the embodiment of the present invention provides the first and second forming sheets capable of (i) accommodating and sealing the development material member, the development medium member and the blocking member therein, (ii) protecting the development material member, the development medium member and the blocking member from an external impact, and (iii) being adhered and deformed under a specific pressure condition to start activation thereof, so that appearances of the development material member, the development medium member and the blocking member can be protected in a state in which the pressure is not applied from the outside, and the development material member can come in contact with the development medium member to start activation thereof when the pressure is applied.

The temperature and time indicator for confirming sterilization according to the embodiment of the present invention includes the blocking member disposed between the development material member and the development medium member and having the through-hole formed in the central section so that the development material comes in contact with only the central section of the development medium member to start the activation thereof from the central portion.

The temperature and time indicator for confirming sterilization according to the embodiment of the present invention informs a user of existence of diffusion through the specific pattern or form printed on the blocking member so that the user can confirm that the product passes through an appropriate sterilization process under a regulated temperature and pressure condition.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 4 is a view showing that the temperature and time indicator 100 for confirming high pressure sterilization according to the embodiment of the present invention is adhered and deformed by an external pressure to start activation thereof, and more specifically, FIG. 4(a) is a view showing a state before the external pressure is applied, and FIG. 4(b) is a view showing first and second forming sheets 140 and 150 adhered and deformed as the external pressure is applied.

DETAILED DESCRIPTION OF EXEMPLARY EMBODIMENTS

Figure 1:
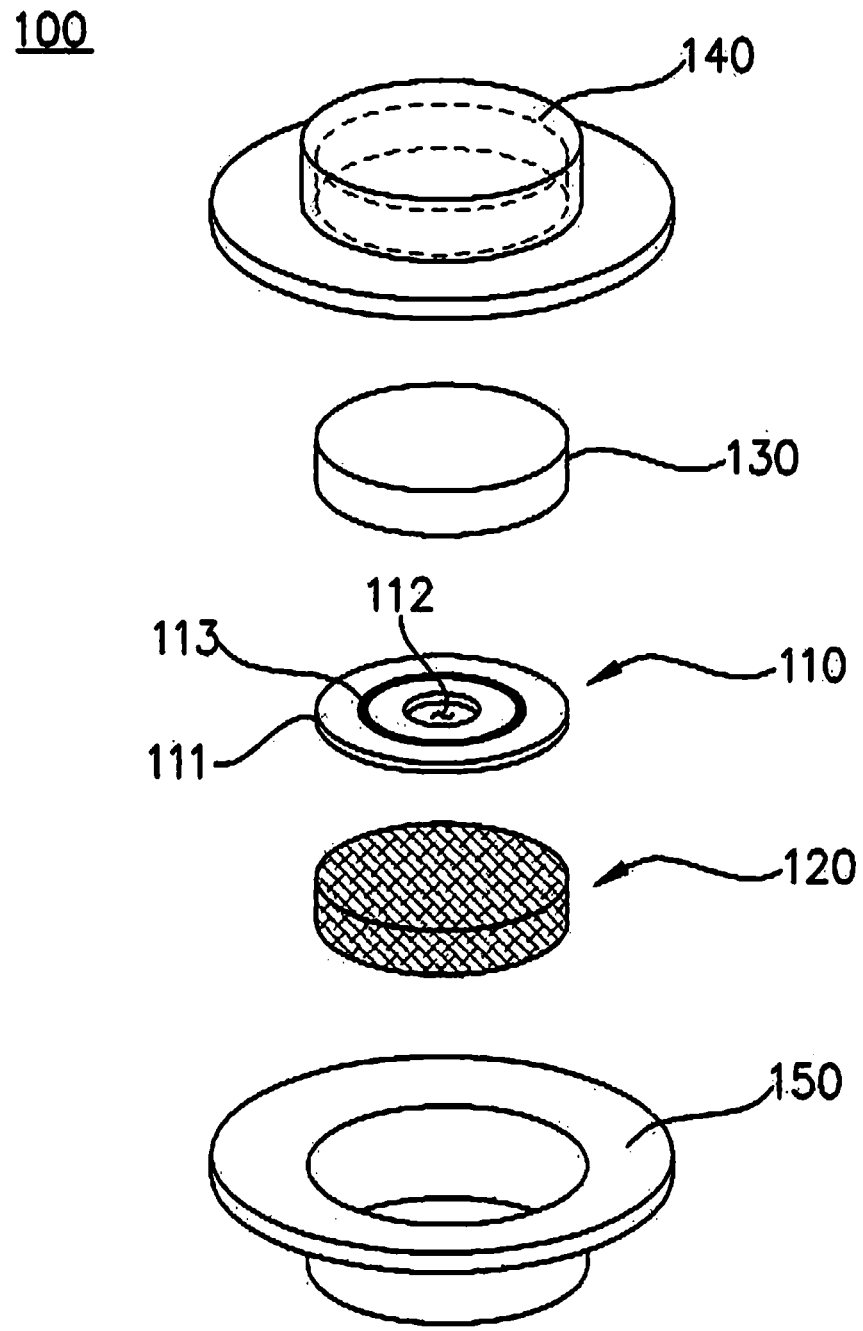
FIG. 1 is an exploded perspective view showing a temperature and time indicator 100 for confirming high pressure sterilization according to an embodiment of the present invention.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

An exemplary embodiment of a temperature and time indicator 100 for confirming high pressure sterilization according to the present invention will be described with reference to the accompanying drawings. In this regard, thicknesses of lines or sizes of components shown in the drawings may be exaggerated for the purpose of clarity and convenience of description. In addition, terms to be described are terms defined in consideration of functions in the present invention and may differ according to intensions or customs of a user or an operator. Accordingly, definitions of these terms should be described based on contents throughout the specification.

Figure 2:
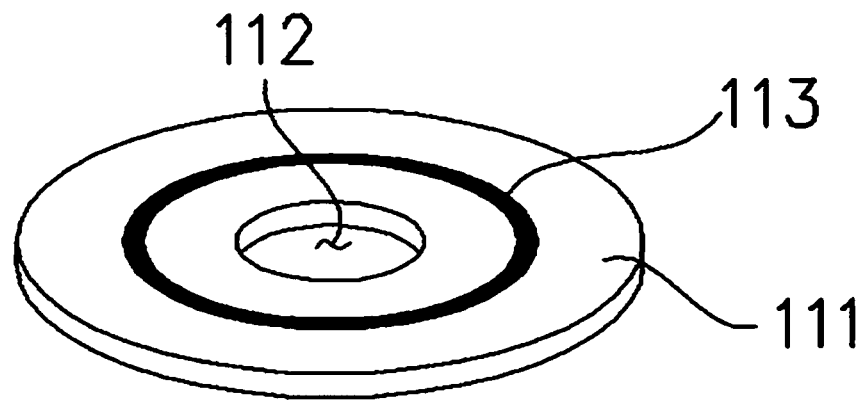
FIG. 2 is a perspective view showing a blocking member 110 shown in FIG. 1.

FIG. 1 is an exploded perspective view showing a temperature and time indicator 100 for confirming high pressure sterilization according to an embodiment of the present invention, and FIG. 2 is a perspective view showing a blocking member 110 shown in FIG. 1.

Referring to FIGS. 1 and 2, the temperature and time indicator 100 for confirming high pressure sterilization includes a blocking member 110, a development material member 120, a development medium member 130, a first forming sheet 140 and a second forming sheet 150.

The blocking member 110 is disposed between the development material member 120 and the development medium member 130, and functions to block the development material member 120 to come in contact with the development medium member 130 in a state in which a specific pressure is not applied.

The blocking member 110 is constituted by a blocking film 111, a through-hole 112 and a sterilization completion mark 113.

The blocking film 111 may have a size equal to or larger than that of the development material member 120, and may have a doughnut shape having a center hole with a predetermined size in a circular plate. Here, if there is no direct contact between the blocking film 111 and the development material member 120, a lateral size of the blocking film 111 is not limited.

The blocking film 111 is formed of a material with no spoilage or deformation even when exposed to a high temperature or a high pressure, or a material into which a development material is not permeated and absorbed. This is to prevent initiation of abnormal activation generated when the development material is absorbed into the blocking film 111 to come in contact with the development medium member 130 disposed at a rear surface thereof. Here, a material of the blocking film 111 is not limited as long as the development material does not permeate and pass through the blocking film 111.

The through-hole 112 is disposed at a center of the blocking film 111, and functions as a path through which a portion of the development material member 120 or the development material passes when a pressure is applied to the outside. Here, a size of the through-hole 112 is not limited as long as a portion of the development material member 120 or the development material passes therethrough. However, the size of the through-hole 112 is smaller than that of the sterilization completion mark 113 to be described below.

The sterilization completion mark 113 is disposed on the blocking film 111, and printed in a specific pattern or form along an outer circumferential surface of the through-hole 112. As the sterilization completion mark 113 is provided, the user can confirm that the product pass through the appropriate sterilization process with the temperature and time indicator 100 for confirming high pressure sterilization. For example, a circle formed on the outer circumferential surface of the through-hole 112 or scales formed at a position spaced a predetermined length from the center of the through-hole 112 may be the sterilization completion mark 113. In addition, the sterilization completion mark 113 may have a color that can be easily checked with the naked eye, and the color of the sterilization completion mark 113 is not limited as long as the color is discriminated with the naked eye.

The development material member 120 is disposed under the blocking member 110, and functions to seal and accommodate the development material melted when exposed to a specific temperature. The development material member 120 such as sponge or non-woven fabric may absorb the development material therein and may be deformed by a pressure to discharge the absorbed development material. Here, in the specification, while it is described that the material of the development material member 120 may be the sponge or non-woven fabric, the material of the development material member 120 is not limited to the sponge or non-woven fabric as long as the development material member 120 can absorb a liquid development material. In addition, a melting point at which the development material is melted may be about 110 to 118 degrees, and the kind of the development material is not limited as long as the development material can be absorbed and diffused in the development medium member 130 to be described below.

The development medium member 130 is disposed on the blocking member 110, and functions to absorb and diffuse the development material discharged from the development material member 120. The development medium member 130 may be formed of a micro-porous film, and may become transparent when comes in contact with the development material. In addition, the development medium member 130 may be formed of a material that is not deformed by the pressure applied from the outside. This is not to exert an influence on existence of diffusion of the development material by deformation upon absorption and diffusion of the development material into the development medium member 130. Here, the material of the development medium member 130 is not limited as long as whether the development material is diffused through the development medium member 130 can be seen from the outside.

The first forming sheet 140 accommodates the blocking member 110 and the development medium member 130 therein, and is deformed when exposed to a specific pressure such that an upper central section thereof is squashed downward. In addition, the first forming sheet 140 has a space configured to accommodate the blocking member 110 and the development medium member 130, and a center of the first forming sheet 140 protrudes upward due to the space. Accordingly, the first forming sheet 140 may have a central section protruding outward.

The second forming sheet 150 accommodates the blocking member 110 and the development material member 120, and is deformed when exposed to a specific pressure (for example, 15 psi) so that a lower central section thereof is squashed downward. In addition, the second forming sheet 150 has a space configured to accommodate the blocking member 110 and the development material member 120, and a center of the second forming sheet 150 protrudes downward due to the space. Accordingly, the second forming sheet 150 may have a central section protruding outward.

The first and second forming sheets 140 and 150 accommodate the blocking member 110, the development material member 120 and the development medium member 130, and function to prevent leakage of the development material discharged from the development material member 120 to the outside. For this, adhered surfaces having a predetermined area are provided at distal ends of the first and second forming sheets 140 and 150. Due to the adhered surfaces, the first and second forming sheets 140 and 150 can surround to seal the blocking member 110, the development material member 120 and the development medium member 130. Here, the area of the adhered surface and the kind of adhesive material are not limited as long as the first and second forming sheets 140 and 150 can seal the blocking member 110, the development material member 120 and the development medium member 130 using the adhered surfaces.

Here, air layers are formed between the first forming sheet 140 and the development material member 120 and between the second forming sheet 150 and the development medium member 130. Accordingly, when the first and second forming sheets 140 and 150 are adhered by the specific pressure, the central section is depressed while contracting the air layer, and thus, the development material member 120 and the development medium member 130 come in contact with each other.

Meanwhile, in FIG. 1, while the central sections of the first and second forming sheets 140 and 150 protrude upward and downward in a rectangular shape so that the blocking member 110 and the development material member 120 are shown as being floated in the air, the actually protruded shape may have a rectangular shape or a circular shape (for example, the first forming sheet 140 may have a shape having a cross-sectional area reduced as it goes upward, or the second forming sheet 150 may have a cross-sectional area reduced as it goes downward. In this case, the blocking member 110, the development material member 120 and the air layers can be naturally maintained at their positions without a separate component or adhering means.

In the embodiment, the first and second forming sheets 140 and 150 may be formed of a transparent material, and thus, the user can confirm the sterilization completion mark 113 from the outside with the naked eye. In addition, while shapes of the first and second forming sheets 140 and 150 are deformed when the specific pressure is applied, spoilage and deformation of the first and second forming sheets 140 and 150 may not occur when exposed to the temperature at which the development material can be melted. This is to prevent the melted development material from coming in contact with the development medium member 130 when the specific pressure is not applied even though the first and second forming sheets 140 and 150 are exposed to the temperature at which the development material can be melted.

Figure 3:
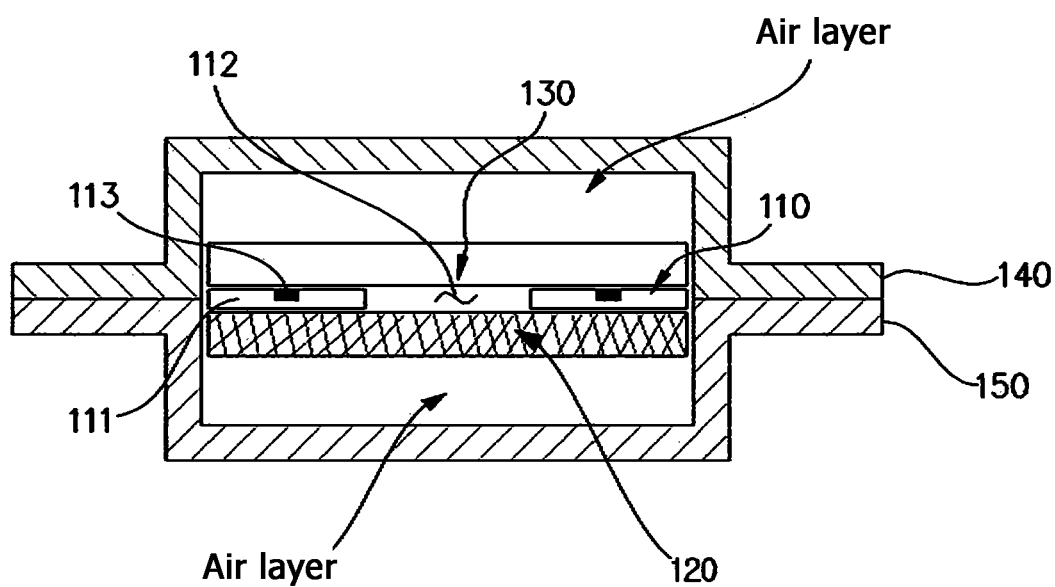
FIG. 3 is a cross-sectional view showing a coupling state of the temperature and time indicator 100 for confirming high pressure sterilization according to the embodiment of the present invention.

FIG. 3 is a cross-sectional view showing a coupling state of the temperature and time indicator 100 for confirming high pressure sterilization according to the embodiment of the present invention.

Referring to FIG. 3, the blocking member 110 is disposed between the development material member 120 and the development medium member 130, and the sterilization completion mark 113 is printed on the blocking film 111 of the blocking member 110.

The development material member 120 is accommodated in the second forming sheet 150, and the development medium member 130 is accommodated in the first forming sheet 140. In addition, portions of the distal ends of the first and second forming sheets 140 and 150 come in contact with each other by the adhered surfaces, and thus, the blocking member 110, the development material member 120 and the development medium member 130 accommodated in the first and second forming sheets 140 and 150 are surrounded and sealed.

FIG. 4 is a view showing that the temperature and time indicator 100 for confirming high pressure sterilization according to the embodiment of the present invention is adhered and deformed by an external pressure to start activation thereof, and more specifically, FIG. 4(a) is a view showing a state before the external pressure is applied, and FIG. 4(b) is a view showing the first and second forming sheets 140 and 150 adhered and deformed as the external pressure is applied.

Referring to FIG. 4, FIG. 4(a) is a view showing a state of the temperature and time indicator 100 for confirming high pressure sterilization before the specific pressure is applied from the outside, and description will be omitted because of similarity to FIG. 3.

Referring to FIG. 4(b), the pressure is applied from the outside to easily attach and deform the first and second forming sheets 140 and 150, and the first and second forming sheets 140 and 150 are compressed and adhered in an inward direction by the applied pressure.

The shape of the development material member 120 is deformed and contracted as the first and second forming sheets 140 and 150 are compressed and adhered, and a portion of the development material member 120 passes through the through-hole 112 formed in the blocking member 110 to come in contact with the development medium member 130. Accordingly, the activation is initiated and the development material melted when exposed to the temperature at which the development material is easily melted is absorbed into the development medium member 130 to be diffused therein.

Here, a portion of the development material member 120 may directly pass through the through-hole 112 to come in contact with the development medium member 130, and the development material absorbed into the development material member 120 may be discharged to be suctioned into the development medium member 130.

As the development material is diffused, the development medium member 130 becomes transparent from the contact point between the development medium member 130 and the development material, and a transparent range is gradually increased. As a result, the sterilization completion mark 113 covered by the development medium member 130 can be seen through the development medium member 130, which becomes transparent. Accordingly, the user can confirm that the product passes through the appropriate high pressure sterilization process.

As described above, the temperature and time indicator 100 for confirming high pressure sterilization includes the first and second forming sheets 140 and 150 adhered and compressed at a specific pressure, the development material member 120 containing the development material melted at a specific temperature, the development medium member 130 configured to absorb and diffuse the development material, and the sterilization completion mark 113 configured to allow a user to visually check whether the development material is diffused, so that the user can easily confirm that the product passes through the appropriate high pressure sterilization process under the regulated temperature and pressure management, and thus, the user can use the product with an easy mind It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A temperature and time indicator for confirming sterilization comprising:
   a development material member configured to melt when exposed to a specific temperature;
   a development medium member configured to absorb and diffuse the development material member;
   a blocking member disposed between the development material member and the development medium member, wherein the blocking member comprises
      a blocking film having a size equal to or larger than a size of the development material member,
      a through-hole disposed at a center of the blocking film, and
      a sterilization completion mark disposed on the blocking film, and printed in a specific pattern or form along an outer circumferential surface of the through-hole; and
   first and second forming sheets configured to accommodate the development material member and the development medium member in upper and lower sides, wherein the first and second forming sheets are compressed and adhered when exposed to a specific pressure;
   wherein the development material comes in contact with the development medium member, through the through-hole formed in the blocking member, to start activation thereof.

2. The temperature and time indicator for confirming sterilization according to claim 1, wherein the through-hole is configured to enable any one or both of the development material member and the development material to pass therethrough.

3. The temperature and time indicator for confirming sterilization according to claim 2, wherein the blocking member has a specific pattern or form printed along an outer circumferential surface of the through-hole.

4. The temperature and time indicator for confirming sterilization according to claim 1, wherein the development material member comprises development material configured to melt at a specific temperature and be absorbed into non-woven fabric.

5. The temperature and time indicator for confirming sterilization according to claim 1, wherein the development medium member comprises a micro-porous film and is configured to become transparent after coming into contact with the development material.

6. The temperature and time indicator for confirming sterilization according to claim 1, wherein the first and second forming sheets have adhered surfaces formed at portions thereof, and the adhered surfaces seal the development material member and the development medium member at upper and lower sides.

7. The temperature and time indicator for confirming sterilization according to claim 6, wherein the first and second forming sheets are not spoiled and deformed even when exposed to a temperature at which the development material is configured to melt.

* * * * *